US010613086B2

(12) United States Patent
Kato et al.

(10) Patent No.: US 10,613,086 B2
(45) Date of Patent: Apr. 7, 2020

(54) HEMOLYTIC *STREPTOCOCCUS* DIAGNOSTIC IMMUNOCHROMATOGRAPHY REAGENT, KIT, AND DETECTION METHOD

(71) Applicant: Tanaka Kikinzoku Kogyo K.K., Tokyo (JP)

(72) Inventors: Yuya Kato, Hiratsuka (JP); Hisahiko Iwamoto, Hiratsuka (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 685 days.

(21) Appl. No.: 14/910,295

(22) PCT Filed: Aug. 8, 2014

(86) PCT No.: PCT/JP2014/071080
§ 371 (c)(1),
(2) Date: Feb. 5, 2016

(87) PCT Pub. No.: WO2015/020210
PCT Pub. Date: Feb. 12, 2015

(65) Prior Publication Data
US 2016/0370368 A1 Dec. 22, 2016

(30) Foreign Application Priority Data
Aug. 8, 2013 (JP) ................. 2013-164819

(51) Int. Cl.
*G01N 33/569* (2006.01)
*G01N 33/558* (2006.01)
(Continued)

(52) U.S. Cl.
CPC ... *G01N 33/56944* (2013.01); *G01N 33/5306* (2013.01); *G01N 33/54393* (2013.01);
(Continued)

(58) Field of Classification Search
CPC ......... G01N 33/5306; G01N 33/54393; G01N 33/558; G01N 33/56944; G01N 2400/10; G01N 2400/18
See application file for complete search history.

(56) References Cited

U.S. PATENT DOCUMENTS 4,673,639 A * 6/1987 Slifkin ................. C12Q 1/14
422/506
4,943,522 A * 7/1990 Eisinger ........... G01N 33/54386
422/537

(Continued)

FOREIGN PATENT DOCUMENTS

EP 0659437 A2 6/1995
EP 1657551 A1 5/2006
(Continued)

OTHER PUBLICATIONS

Roberts, "The Biochemistry and Genetics of Capsular Polysaccharide Production in Bacteria", Annu. Rev. Microbiol. 1996, 50:285-315. (Year: 1996).*

(Continued)

*Primary Examiner* — Christopher L Chin
(74) *Attorney, Agent, or Firm* — Orrick, Herrington & Sutcliffe LLP; Joseph A. Calvaruso; K. Patrick Herman

(57) ABSTRACT

Disclosed herein is an immunoassay method for detecting the detection target antigen in an analyte through extraction with an extraction agent. The method is characterized in that the detection is performed in the presence of a cyclic oligosaccharide. The method is also characterized in the use of an immunochromatography kit for detecting gram-positive bacteria in an analyte, and that is configured from an analyte dilution solution, a sample dropping part, an antigen extracting part, a labeling substance retaining part, an immunochromatography medium having a detection part, and an absorption part, and in which an organic acid is retained in (Continued)

the antigen extracting part. The immunochromatography kit contains a cyclic oligosaccharide and a nitrite compound by containing at least one of a cyclic oligosaccharide, a nitrite compound, and a mixture thereof in the analyte dilution solution and/or the sample dropping part.

8 Claims, 2 Drawing Sheets

(51) Int. Cl.
G01N 33/53 (2006.01)
G01N 33/543 (2006.01)

(52) U.S. Cl.
CPC ....... *G01N 33/558* (2013.01); *G01N 2400/10* (2013.01); *G01N 2400/18* (2013.01); *G01N 2469/10* (2013.01)

(56) References Cited

U.S. PATENT DOCUMENTS

| | | | | |
|---|---|---|---|---|
| 5,536,646 | A | * | 7/1996 | Sand ........................ C12Q 1/14 424/718 |
| 5,670,381 | A | * | 9/1997 | Jou ....................... G01N 33/538 435/7.92 |
| 5,770,458 | A | * | 6/1998 | Klimov ................. G01N 33/543 422/110 |
| 2004/0175695 | A1 | | 9/2004 | Debad et al. |
| 2008/0206849 | A1 | * | 8/2008 | Zak ....................... G01N 33/558 435/287.2 |
| 2013/0011932 | A1 | | 1/2013 | Itoh et al. |

FOREIGN PATENT DOCUMENTS

| | | |
|---|---|---|
| EP | 1980853 A1 | 10/2008 |
| JP | H01-153961 A | 6/1989 |
| JP | H02-040559 A | 2/1990 |
| JP | H05-209878 A | 8/1993 |
| JP | H07-503543 A | 4/1995 |
| JP | H07-278184 A | 10/1995 |
| JP | H08-248030 A | 9/1996 |
| JP | H11-083855 A | 3/1999 |
| JP | H11-248706 A | 9/1999 |
| JP | 2002-503812 A | 2/2002 |
| JP | 2004-109062 A | 4/2004 |
| JP | 2006-518990 A | 8/2006 |
| JP | 2007-315883 A | 12/2007 |
| JP | 2008-509384 A | 3/2008 |
| JP | 2009-036781 A | 2/2009 |
| JP | 2011-141252 A | 7/2011 |
| JP | 2012-251789 A | 12/2012 |

OTHER PUBLICATIONS

PCT, International Search Report PCT/JP2014/071080, dated Nov. 11, 2014.
EP, Office Action for European application No. 14834355.1, dated Jan. 5, 2018.
EP, Extended European Search Report concerning 14834355.1, dated Feb. 17, 2017.
CN, Office Action for Chinese application No. 201480045105.7, dated Aug. 16, 2017.

* cited by examiner

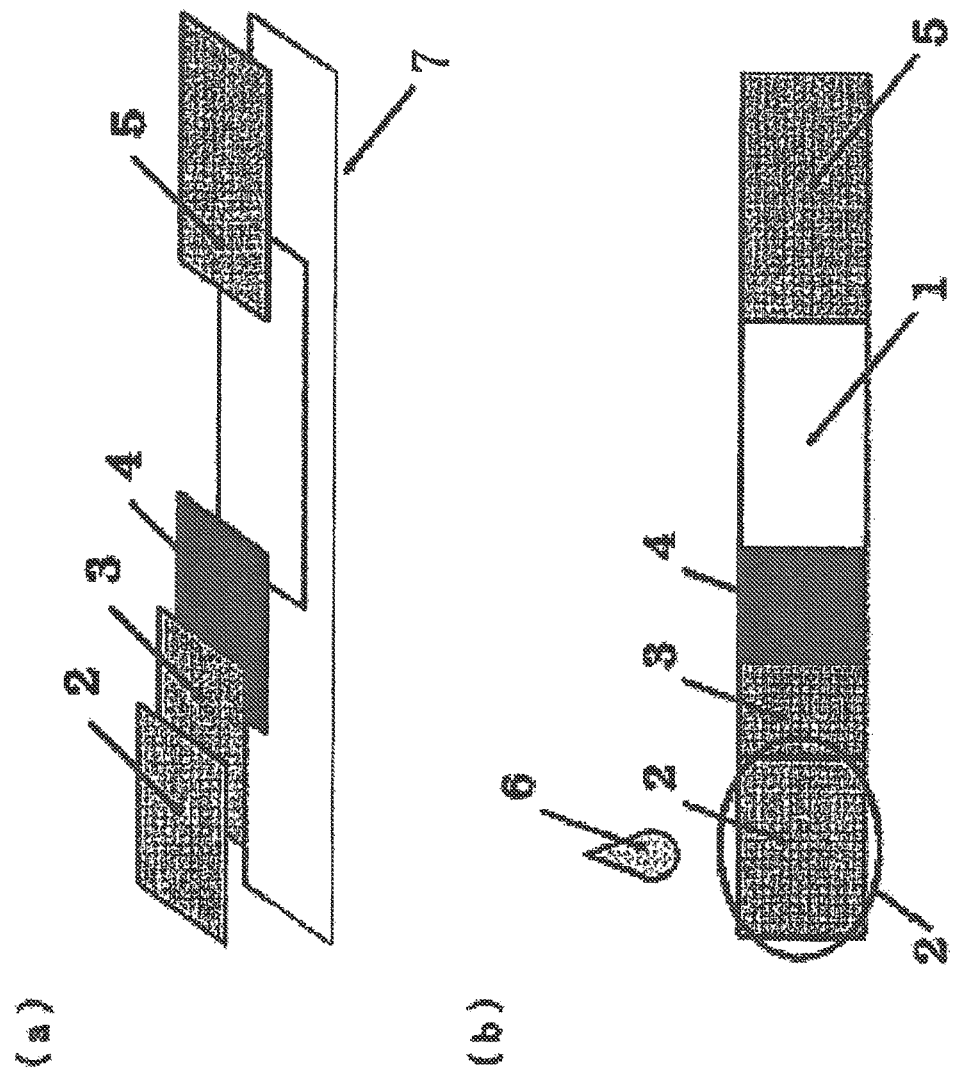
[FIG.1]

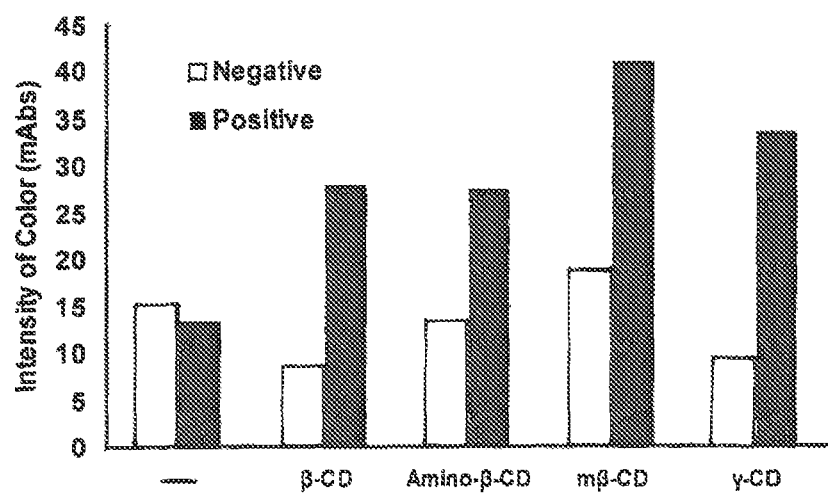
[FIG.2]

HEMOLYTIC *STREPTOCOCCUS* DIAGNOSTIC IMMUNOCHROMATOGRAPHY REAGENT, KIT, AND DETECTION METHOD

TECHNICAL FIELD

The present invention relates to an immunochromatography kit having great importance as a simple in vitro diagnostic kit or a portable diagnostic device that detects gram-positive bacteria, particularly hemolytic streptococci, as a substance to be detected (e.g., antigens) in a sample liquid; a reagent composition; an analyte treatment solution and a detection method for use in the kit. The invention particularly relates to a test method that improves the efficiency and accuracy of testing by producing a nitrous acid, needed for the extraction of the necessary polysaccharides in a streptococcus test, on a test device without having to prepare it at the time of use for each testing.

BACKGROUND ART

A strip-type immunoassay for immunochromatography has become widely applicable as a simple in vitro diagnostic kit or a portable diagnostic device that makes use of specific reactivity of antibodies to detect a substance to be detected (e.g., antigens) in a sample liquid. A simple immunochromatographic testing instrument for testing the presence or absence of an infection caused by pathogens such as influenza virus and bacteria has attracted interest, and there has been ongoing research and development of such instruments.

Diagnosis of hemolytic streptococcus (hereinafter, also referred to as "streptococcus") is performed using group specific polysaccharides as antigens. Known polysaccharide extraction methods include methods using enzymes or phages, and methods using hydrochloric acid or hypochlorous acid. The extraction method using nitrous acid is most common.

The extraction method using nitrous acid has merits in its high polysaccharide extraction efficiency, and the low price and easy handling of nitrous acid. A demerit is that a nitrous acid itself is an unstable compound that easily decomposes, and needs to be prepared for each use by mixing sodium nitrite and organic acids such as acetic acid prior to extraction. Such preparation of a nitrous acid puts a large burden on physicians and laboratory technicians when diagnosis needs to be made regularly. Another drawback is that, because of the mixing step, an error may occur in mixing the reagents, and the method may fail to properly and safely perform diagnosis.

In order to overcome these problems, there has been research and development of simple testing instruments that simplify the step of extracting polysaccharide antigens from streptococci.

For example, Patent Document 1 proposes a method for extracting polysaccharide antigens from organisms (particularly, Group A or B streptococci). The method simplifies the extraction with the use of a kit that combines a) a dry first absorbent material impregnated with a premeasured amount of nitrite, b) a dry second absorbent material impregnated with a premeasured amount of a neutralizing base and buffer, and c) a premeasured amount of an aqueous solution of an acid (see Patent Document 1).

Diagnosis of a streptococcal infection requires the complicated process of performing a polysaccharide antigen extraction step, followed by an antigen detection step in which the resulting solution is contacted to an immunoassay device. There accordingly remains the challenge of developing a method or a kit therefor for conveniently measuring and testing organisms in a sample with a polysaccharide antigen extraction step, and a marker measurement step.

For example, Patent Document 2 discloses an assay device and method for the detection of carbohydrate antigens characteristic of microbial/bacterial organisms such as the family Streptococcaceae. This lateral flow assay device includes a substrate having a) sample receiving zone, b) an extraction zone (extraction reagent; an immobilized or absorbed, and dried acid or nitrite), c) a neutralizing agent (neutralizing buffer; TRIS), and d) a detection zone (capture/detection reagent) (see Patent Document 2).

A method and a kit therefor for simultaneously measuring and testing different organisms containing streptococci are also developed.

For example, Patent Document 3 discloses a method and a kit for measuring a plurality of different biological species in a sample, such as in a sample containing a first organism that is a gam-positive bacterium, for example, such as Group A, B, F, or G streptococeus, and enterococcus bacteria, and a second organism that is a virus or a gram-negative bacterium. The simultaneous detection of a plurality of analytes is enabled by a kit that includes, in one or more containers, a) a nitrous acid, or a dry form of an acid or a nitrite, b) a surfactant, c) a first binding reagent that binds to a first marker obtained from the first organism, and d) a second binding reagent that binds to a second marker obtained from the second organism. This achieves doubling of test efficiency and alleviation of pain caused to patients by the test (see Patent Document 3).

An assay device and method for the detection of carbohydrate antigens characteristic of microbial/bacterial organisms such as the family Streptococcaceae is commercially available. For example, QuickVue DipStick Strep A (DS Pharma Biomedical), and Strep A TestPack-plus OBC (Sanwa Kagaku Kenkyusho) are known examples of immunochromatography reagents. Known examples of slidelatex agglutination reagents include A Strept AD "Seiken" (Denka Seiken).

In order to produce a positive result in common testing of an analyte, a commercially available immunochromatography reagent requires a streptococcus concentration of at least $1\times10^6$ CFU/mL, in the direct method. The test thus may identify a positive specimen as negative when the streptococcus concentration is below $1\times10^5$ CFU/mL. An immunochromatographic test agent using antibodies labeled with an insoluble support is typically less sensitive than EIA, and involves such problems that an unclear line is observed in a positive case, and a positive result is provided even in the absence of a substance to be detected (e.g., antigens) in a sample liquid (i.e., false positive result is caused).

These problems are addressed by methods that use sugars or water-soluble high molecular compounds in a developing solvent. For example, a membrane assay is proposed that uses antibody-conjugated color latex particles. The assay uses an immunoassay latex composition of pH 9.0 to 9.8 containing at least one agglutination preventing agent such as sugars (for example, monosaccharides, and oligosaccharides, and sugar alcohols of such sugars) and polyalcohol; proteins; and a basic buffer. The composition prevents natural agglutination of latex particles, and increase of specific gravity, viscosity, and osmotic pressure to achieve high sensitivity immunoassay (see Patent Document 4).

In addition, recently, concerning a particle immunochromatography assay of glycohemoglobin (blood hemoglogin with the bound sugar) used an a suitable index of diabetes diagnosis, particularly hemoglobin A1c (HbA1c) with the glycosylated N-terminal valine residue in the hemoglobin β chain, there is proposed a detection method that includes (A) treating a red blood cell-containing measurement sample with a surfactant to expose the N-terminal of hemoglobin β chain on protein surface, (B) contacting the resulting sample to a cyclic polysaccharide of water-insoluble form (for example, a cyclic polysaccharide is immobilized on a membrane or the like by chemically bonding, a cyclic polysaccharide itself forms a polymer, or a cyclic polysaccharide is kneaded in a porous resin), and (C) contacting the resulting sample to antibodies or the like that recognize the N-terminal of the particle-labeled hemoglobin. In this way, the antibodies are prevented from agglutinating each other and failing to develop on the membrane, and the method prevents measurement inaccuracy caused when the constituent cyclic oligosaccharide molecule or cyclic polysaccharide molecule of the cyclic polysaccharide does not dissolve in water and does not diffuse upon contacting water (see Patent Document 5).

Concerning a simple method of testing an analyte using membrane assay, there is proposed an analyte sample filtration method that enables preventing yielding a false positive result or clogging while maintaining sensitivity (see Patent Document 6).

However, the immunochromatography technique (also referred to as "particle immunochromatography technique") using antibodies labeled with an insoluble support (e.g., gold colloidal particles, and color latex particles) still involves agglutination of the insoluble support, and, possibly, non-specific reactions, depending on the measurement sample, the measurement environment, and the measurement conditions. Problems such as slow development rate may thus still remain. There accordingly is a strong need for pursuit of a test agent having a fast development rate and that does not cause agglutination of insoluble support or non-specific reactions even when used in the particle immunochromatography technique with different measurement samples under different measurement environments and conditions.

CITATION LIST

Patent Documents

Patent Document 1: JP-T-7-503543
Patent Document 2: JP-T-2008-509384
Patent Document 3: JP-T-2006-518990 (Japanese Patent No. 4667874)
Patent Document 4: JP-A-2007-315883
Patent Document 5: JP-A-2012-251789
Patent Document 6: JP-A-2009-36781

SUMMARY OF THE INVENTION

Problems to be Solved by the Invention

A purpose or an object of the present invention is to provide a high-sensitivity test agent for immunochromatography that reduces color production in a negative analyte and improves color production in a positive analyte (i.e., provides a high S/N ratio) in a development system over the related art through improvement of a sample extraction (dilution) solution (also referred to as "analyte treatment solution" or "development solution") used for immunochromatographic testing of gram-positive bacteria, particularly streptococci.

Another object of the present invention is to provide a high sensitivity test agent having a high development rate that, trough improved development and extraction conditions, enables development and detection without causing denaturation or deposition (settling) of the protein component present in an analyte or in an immunochromatography device in immunochromatographic testing of bacteria.

A further object of the present invention is to provide an immunoassay reagent, an immunoassay method, an immunochromatographic detection method, and an immunochromatography kit that, through improvement of the configuration at the attachment site of the immunochromatography kit, enable faster and more accurate testing of microorganisms in a sample (for example, an analyte collected from a respiratory disease patient, particularly from nasal discharge, a swab from nasal cavity, or phlegm) or antigens or antibodies originating in microorganisms (for example, bacteria such as gram-positive bacteria, particularly hemolytic streptococci) than the related art in immunochromatographic testing of bacteria. Specifically, a streptococcus test requires extraction of polysaccharides with a nitrous acid, and the unstable compound nitrous acid needs to be prepared at the time of use for each testing through the complicated nitrous acid generating step that involves reaction of a nitrite with an acidic solution. The present invention generates a nitrous acid in the presence of a cyclic oligosaccharide on a test device, instead of preparing a nitrous acid at the time of use for each testing, and can thus improve the test efficiency, the test accuracy, and the power efficiency of the immunoassay reagent, the immunoassay method, the immunochromatographic detection method, and the immunochromatography kit.

Specifically, it is an object of the present invention is to provide an easy and high sensitivity (high S/N ratio) sample extraction solution (hereinafter, also referred to as "sample dilution solution"); reagent for immunochromatography that enable a quick diagnosis of group A β-hemolytic streptococcus as one of respiratory infections; and an immunochromatography kit and a test method using the solution and the reagent.

Means for Solving the Problems

For the testing of bacteria with an immunochromatographic test agent, the present inventors contained a cyclic oligosaccharide and/or a nitrite in a sample extraction solution to be used, or in a reagent retaining part disposed upstream of another reagent retaining part retaining an organic acid in an immunochromatography kit relative to the sample development direction. The present inventors found, for the first time, that this enables providing a test agent having high test accuracy (hereinafter, "S/N ratio") and a high development rate, and that does not induce non-specific reaction or agglutination of antibody-immobilized particle colloids, which occurs when substances such as protein components in an analyte or an immunochromatography device denature or deposit, and become trapped at the determination line even if the retained organic acid or the generated nitrous acid changes the pH condition of the development solution as the sample extraction solution during the development in the test device.

The detection system of the present invention provides an immunoassay reagent, an immunoassay method, and an immunochromatography kit or the like that, by addition of a cyclic oligosaccharide, enable testing without causing deposition of substances such as the protein components in the extraction solution and the analyte in the device even under the development/extraction conditions in which an organic acid is contained as a reagent component, and a nitrous acid is generated.

The present invention is intended to provide an analyte treatment solution, an immunoassay reagent, an immunoassay method, an immunochromatographic detection method, and an immunochromatography kit for use in the immunochromatography method concerning (1) to (19) below. The invention is also intended to provide an immunochromatography method using these.

The immunoassay method of the present invention has the following characteristics.

(1) The first characteristic of the present invention is an immunoassay method for detecting an antigen of a detection target in an analyte through extraction with an extraction agent, which comprises performing the detection in the presence of a cyclic oligosaccharide.

(2) The second characteristic of the present invention is the immunoassay method in which the extraction agent is nitrous acid that generates on a device through reaction of an organic acid and a nitrite compound.

(3) The third characteristic of the present invention is the immunoassay method in which the cyclic oligosaccharide is α-cyclodextrin, β-cyclodextrin, γ-cyclodextrin, and a derivative thereof.

(4) The fourth characteristic of the present invention is the immunoassay method in which the nitrite compound is a nitrite.

(5) The fifth characteristic of the present invention is the immunoassay method in which the organic acid is an organic carboxylic acid.

(6) The sixth characteristic of the present invention is the immunoassay method in which the extraction is performed under a pH condition with a pH of less than 7.0 to 6.5.

(7) The seventh characteristic of the present invention is the immunoassay method in which the antigen is a polysaccharide.

(8) The eighth characteristic of the present invention is the immunoassay method in which the detection target is a gram-positive bacterium.

(9) The ninth characteristic of the present invention is the immunoassay method in which the grave-positive bacterium is a hemolytic streptococcus.

The immunoassay reagent of the present invention has the following characteristic.

(10) The tenth characteristic of the present invention is an immunoassay reagent for use in any one of the immunoassay methods described above, which comprises a cyclic oligosaccharide.

The immunochromatography device of the present invention has the following characteristic.

(11) The eleventh characteristic of the present invention is an immunochromatography device for performing any one of the immunoassay methods described above.

The immunochromatography kit of the present invention has the following characteristics.

(12) The twelfth characteristic of the present invention is an immunochromatography kit for detecting a detection target in an analyte, which comprises: an analyte dilution solution; a sample dropping part; an antigen extracting part; a labeling substance retaining part; a chromatography medium having a detection part; and an absorption part, the antigen extracting part having an organic acid retained therein, in which the kit contains a cyclic oligosaccharide and a nitrite compound by containing at least one of a cyclic oligosaccharide, a nitrite compound, and a mixture thereof in the analyte dilution solution and/or the sample dropping part.

(13) The thirteenth characteristic of the present invention is the immunochromatography kit in which the cyclic oligosaccharide is contained in 0.1 to 5 μg per immunochromatography kit.

(14) The fourteenth characteristic of the present invention is the immunochromatography kit in which the cyclic oligosaccharide is at least one of α-cyclodextrin, β-cyclodextrin, γ-cyclodextrin, and a derivative thereof.

(15) The fifteenth characteristic of the present invention is the immunochromatography kit in which the organic acid is retained with a non-ionic surfactant.

(16) The sixteenth characteristic of the present invention is the immunochromatography kit in which the nitrite compound is a nitrite.

(17) The seventeenth characteristic of the present invention is the immunochromatography kit in which the antigen extracting part retains citric acid with a citrate.

(18) The eighteenth characteristic of the present invention is any one of the immunochromatography kit described above in which the detection target is a gram-positive bacterium.

(19) The nineteenth characteristic of the present invention is the immunochromatography kit which is used to perform any one of the immunoassay method described above.

The present invention has achieved the objectives with the features set forth above.

Effect of the Invention

The present invention uses a nitrous acid that generates upon contacting and mixing premeasured amounts of nitrite compound and organic acid to extract group-specific polysaccharides present on the bacteria surface of gram-positive bacteria, specifically streptococci (Group A to Group U), and uses the polysaccharides as antigens for testing. The invention can thus provide an easy and versatile test kit and method that does not involve an error in mixing reagents, or require preparation of a nitrous acid for each testing. A streptococcus detection system using the immunochromatography kit of the present invention, by addition of a cyclic oligosaccharide, enables high-sensitivity and quick testing without causing deposition of the protein components in the extraction solution and the analyte even under extraction/development conditions.

Specifically, the present invention, with the use of a sample extraction solution (also referred to as "analyte dilution solution") for immunochromatography containing a cyclic oligosaccharide, enables providing a test agent that is accurate and has a fast development rate, without depositing proteins or causing agglutination of antibody-immobilized gold colloidal particles during the development. Further, the present invention, by containing a cyclic oligosaccharide in a separate reagent retaining part, enables quickly and conveniently determining the test result with high sensitivity without causing denaturation or settling of antigens (for example, gram-positive bacteria, particularly streptococci) in a sample such as an analyte collected from a respiratory disease patient (particularly, a sample from nasal discharge, a swab from nasal cavity, or phlegm) even under the conditions in which an acid is retained in the reagent retaining part, and a nitrous acid is generated.

The invention also can provide a test method having improved test efficiency and accuracy that does not require the complicated nitrous acid generating step of reacting a nitrite with an acidic solution at the time of use for each testing, but instead generates a nitrous acid on a test device to eliminate the complexity of such a test.

BRIEF DESCRIPTION OF DRAWINGS

FIG. 1 is a diagram representing an immunochromatography kit of the present application. FIG. 1 (a) is a three-dimensional perspective view of the immunochromatography kit FIG. 1 (b) is a plan view of the immunochromatography kit.

FIG. 2 is a diagram representing the color changing behavior of negative analytes and positive analytes with various cyclodextrin (CDs) contained in a nitrous acid-containing part.

EMBODIMENTS FOR CARRYING OUT THE INVENTION

The present invention is described below in detail. In the present invention, "mass" means "weight."

An embodiment of the present invention is based on an immunochromatography method, or a detection method using same, whereby a detection target (antigen) as a substance to be detected in various analytes is reacted with a specific binding substance (antibody) conjugated to various labels in an antigen-antibody reaction on a chromatography medium to form a complex, developed toward the absorption site on the immunochromatography medium, and confirmed with various detection means. As the antibody that most specifically reacts and binds to the antigen, for example, a monoclonal antibody, a polyclonal antibody, or any other known antibody that specifically binds to the antigen may be used.

As the label, any of enzymes, chromogenic substances, fluorescent substances, and radioactive substances may be used. The label may be selected to exploit the easy operation and the short detection time of the immunochromatography method, taking also into consideration the types of antibodies and antigens.

In addition, the detection means is characterized by its performance to enable accurate determination through visual inspection so that the immunochromatography method can exhibit its easy operation and relatively short determination time. However, when time and accuracy are of concern, other detection means may additionally be used to perform detection, for example, such as by spectrophotometric means, or by detecting radiation.

The following describes the best mode of implementing the analyte dilution solution (also referred to as "analyte treatment solution"), the immunoassay reagent, the immunoassay method, the immunochromatographic detection method, and the immunochromatography kit usable for the immunochromatography method of the present invention, in order.

The immunoassay reagent of the present invention is a reagent used for immunoassay, and is used by being contained in an analyte dilution solution (6) (also referred to as "analyte treatment solution", or "analyte extraction solution") and/or by being contained and retained in a sample dropping part (2) (also referred to as reagent retaining part (2)). The immunoassay reagent may additionally be contained and retained in at least one site selected from a reagent retaining part (3) (also referred to as "antigen extracting part" (3)), a labeling substance retaining part (4), and a chromatography medium (1). When contained in the analyte dilution solution or the sample dropping part, the reagent has the property to migrate and develop from the organic acid-containing antigen extracting part (reagent retaining part (3)) to the labeling substance retaining part (4) and to the chromatography medium (1) and the absorption part (5) in order.

As the immunoassay reagent of the present invention, a cyclic oligosaccharide and a nitrite compound is (are) contained, either alone or together, in at least one of the analyte dilution solution (6) and the reagent retaining part (2). The cyclic oligosaccharide and the nitrite compound forming the immunoassay reagent may be contained in the analyte extraction solution or kept in the sample dropping part (reagent retaining part (2)) in the following embodiments.

The following represents detailed and specific examples of embodiments of the component and the constituent site containing the nitrite compound (or "NC" for short) and the cyclic oligosaccharide (or "CO" for short) of the present invention. Given below are possible embodiments (patterns) in which the NC and CO compounds are contained in the analyte dilution solution (analyte treatment solution) (6) and the sample dropping part (reagent retaining part (2)), respectively.

| Pattern | Analyte dilution solution (extracting solution) part (6) | Sample dropping part (2) |
| --- | --- | --- |
| 1 | None | NC and CO |
| 2 | NC | CO |
| 3 | CO | NC |
| 4 | NC and CO | None |
| 5 | NC and CO | NC and CO |
| 6 | NC and CO | NC |
| 7 | NC | NC and CO |
| 8 | CO | NC and CO |
| 9 | NC and CO | CO |

The present invention can be implemented in these embodiments (patterns).

The reagent in the sample dropping part (reagent retaining part (2)) may be a solution form, or a form retained in a dropping pad by freeze drying.

The content of the cyclic oligosaccharide constituting the immunoassay reagent of the present invention is 0.1 to 5 μg/test per immunochromatography kit.

The nitrite compound of the present invention is preferably a nitrite. The nitrite compound is not particularly limited, and may be an inorganic nitrite, for example, such as sodium nitrite, potassium nitrite, calcium nitrite, and magnesium nitrite, or an organic nitrite compound, for example, such as methyl nitrite, ethyl nitrite, butyl nitrite, and amyl nitrite, as long as it generates a nitrous acid through reaction with an acid, and does not cause adverse effects on a test in the test device system. These may be used as a mixture. Preferred are inorganic nitrites. Among them, alkali metal salts of nitrous acids are preferred, and sodium nitrite is most preferred.

The content of the nitrite compound contained in the immunoassay reagent is 10 to 100 μmol/test, preferably 20 to 80 μmol/test.

The cyclic oligosaccharide used in the present invention is not particularly limited, as long as it is an oligosaccharide of a structure in which ID-glucose and/or derivatives thereof are linked by α(1→4) glucosidic bonds in a ring. Specific examples include cyclodextrin, for example, α-cyclodextrin, β-cyclodextrin, and γ-cyclodextrin; α-, γ- or γ-) cyclodextrin derivatives such as hydroxyalkylated cyclodextrin, sulfoalkylated cyclodextrin, monochlorotriazinyl cyclodextrin, cluster cyclodextrin, and modified cluster cyclodextrin; and cyclic glucans such as cycloamylose of about 20 to 50 glucose molecules bonded to form a ring, laurylated cycloamylose, and water-soluble xylans derived form cycloamylose. These cyclodextrin and cyclic glucans may be used as a mixture. Among them, preferred is at least one kind selected from β-cyclodextrin and γ-cyclodextrin (see JP-A-2012-188573, and JP-A-2012-251789).

Cyclic oligosaccharides generally have a unique structure with a hydrophilic outer cyclic structure, and a hydrophobic (lipophilic) inner cyclic structure. Because of this unique structure, cyclic oligosaccharides can form a complex by enveloping a lipophilic molecule that is smaller than the inner diameter of their cyclic structures. It is also known that cyclic oligosaccharides can also form such a complex with molecules larger than the inner diameter of their cyclic structures by incorporating a lipophilic portion smaller than the inner diameter of the cyclic structure, when such a lipophilic portion is present in the molecules.

In the present invention, a hydrocarbon functional group as a lipophilic moiety of an organic acid molecule is incorporated in the cyclic oligosaccharide, and inhibits formation of a complex between the organic acid and the protein component in the substance to be detected, or protein components derived from other biological substance in a sample, or protein components contained in additives or the like of the immunochromatography kit. This makes it possible to inhibit non-specific reaction due to the complex formation, and development errors such as low development rate and development failure caused by deposition of the complex.

It is particularly preferable that the cyclic oligosaccharide present in the immunoassay reagent of the present invention is α-cyclodextrin, β-cyclodextrin, γ-cyclodextrin, or a derivative of these.

The cyclic oligosaccharide is used in preferably 0.02 to 0.5 μmol per test.

The test sample used in the present invention is preferably a sample containing gam-positive bacteria with a thick peptidoglycan layer. Examples of such gram-positive bacteria include staphylococci, streptococci, pneumococci, bacilli, *Bacillus anthracis, Bacillus cereus, Corynebacterium diphtheriae, Listeria, Clostridium tetani, Clostridium botulinum*, and *Clostridium perfringens*. The kit of the present invention is used more preferably for samples containing cocci, specifically staphylococci, streptococci, and pneumococci, optimally streptococci.

The samples containing gram-positive bacteria are not particularly limited, and may be, for example, biological samples such as saliva, nasal discharge, a swab from nasal cavity, a fluid withdrawn from nasal cavity, phlegm, a swab from pharynx, an alveolar lavage fluid, a swab from rectum, a fecal suspension, urine, and an amniotic fluid, or samples such as a food extract, clean water, wastewater, and a culture. The invention is useful when the causal bacteria contained in these analytes are gram-positive bacteria, particularly bacteria containing streptococci. The detection system of the present invention characterized by addition of a cyclic oligosaccharide is applicable to bacteria from which antigen polysaccharides specific to the bacteria can be extracted with the generated nitrous acid. The gram-positive bacteria to be detected with the immunochromatography kit of the present invention are specifically hemolytic streptococci.

The immunochromatographic detection of the present invention using a cyclic oligosaccharide can inhibit the denaturation or deposition of high-viscosity proteins contained in nasal discharge or other such analytes, proteins or the like present on the test device caused by the organic acid or by the nitrous acid generating in the detection system. This makes it possible to prevent clogging of the pores in the chromatography material, and thus lowering of the development rate. Because the viscosity increase due to components such as high-viscosity proteins is also inhibited, a high speed development without accompanying sensitivity decrease and a fast analyte detection become possible.

Next, the immunoassay method of the present invention is characterized in that the detection target antigen in a sample is extracted with an extraction reagent, and detected in the presence of a cyclic oligosaccharide. This characteristic of the immunoassay method lies in the extraction reagent being generated as a nitrous acid on the test device, particularly in the organic acid-containing antigen extracting part (reagent retaining part (3)), through reaction of the organic acid and the nitrite compound.

The organic acid is an organic carboxylic acid. Preferably, the immunoassay method is performed with the organic acid retained with the non-ionic surfactants below.

The extraction reagent, produced as a nitrous acid through reaction of the organic acid and the nitrite compound, has an extraction pH of preferably less than 7.0 to 6.5. This is for the following reasons.

The antigen used in the immunochromatographic detection of streptococcus is typically a group-specific polysaccharide present on bacteria surface. Antigen extraction by nitrous acid offers much higher extraction efficiency than extraction using an extraction solution containing various enzymes. However, problems occur when the acid retained in the reagent retaining part, or the generated nitrous acid makes the pH condition acidic during the development. Specifically, proteins, for example, such as casein, or salts thereof, and high-viscosity proteins contained in the analyte in the immunochromatographic detection system become deposited.

In a multidimensional study of common extraction solutions [1) enzyme, 2) added salt, 3) surfactant, 4) ionic liquid, 5) (nitrous acid-producing) catalyst, 6) nitrous acid], the present invention focused on behaviors of 1) enzyme, and confirmed, rather unsurprisingly, that the extraction solution systems 1) to 5) had lower antigen extraction efficiency than 6) nitrous acid. Nitrous acid was thus considered necessary for antigen extraction. However, nitrous acid generates in acidic conditions, and the protein casein in common extraction solutions deposits in acidic conditions, and therefore, combination use is very difficult. The present invention thus searched for acidic conditions strong enough to generate nitrous acid but sufficiently weak to cause deposition of casein.

[Behaviors of System Using Common Extraction Solution and Nitrous Acid]

|  | pH | | | | |
| --- | --- | --- | --- | --- | --- |
|  | 6 | 6.5 | 6.8 | 7 | 8 |
| Bubbles (Nitrous acid) | Present | Present | Slightly present | None | None |
| Settling (Casein) | Present | Slightly present | None | None | None |

It was found from these analysis results that a pH of about 6.5 to 7 was sufficient to allow co-use of a nitrous acid and a common extraction solution. In order to improve antigen extraction efficiency, the present invention investigated what improvements were needed to achieve this from the perspective of both common extraction solution and kit configuration, as follows.

After further studies and research on this issue, the pH condition that generates a nitrous acid but does not deposit proteins such as casein, and high-viscosity proteins or the like contained in the analyte was found to be a pH of less than 7.0 to 6.5, preferably less than 7.0 to 6.6, most preferably less than 7.0 to 6.8 in the present invention. With a pH condition of less than 7, the nitrous acid generation is not reduced and the antigen extraction efficiency is not lowered, and therefore detection sensitivity does not deteriorate. With a pH condition of 6.5 or more for generating a nitrous acid, there is no possibility of causing deposition of proteins such as casein, and high-viscosity proteins or the like contained in the analyte, and a detection failure can be avoided.

The immunochromatography kit of the present invention is designed such that an analyte is developed in neutral to weakly acidic conditions to generate a nitrous acid. This design still enables testing with existing extraction solutions used for other respiratory infections. However, non-uniform development occurs because the component (casein) contained in the extraction solution deposits in weakly acidic conditions. In order to solve this problem, the present inventors conducted studies to reduce deposition of such components by adding various compounds.

It was found as a result that deposition of components can be reduced, and the uniformity of the development can improve when a cyclic oligosaccharide is contained, for example, in the nitrite containing part or in the analyte dilution solution in the detection system.

It was confirmed that it is preferable to conduct the development under neutral to weakly acidic conditions (pH=6.8) as a condition for nitrous acid generation to properly implement the present invention. This design condition can accommodate testing with existing extraction solutions used for respiratory infections.

However, a problem remains that the component (casein) contained in the extraction solution deposits under weakly acidic conditions, and the non-uniform development occurs. As a result of a study directed to reducing deposition of such components by adding various compounds in order to reduce deposition of such components, it was revealed that deposition of components can be reduced, and that uniformity of the development can be improved when cyclodextrin (CD), particularly the well-known β-cyclodextrin (β-CD) is contained. The following trend was observed. Note: BSA stands for bovine serum albumin, PEG stands for polyethylene glycol (PEG 20000), and TH stands for trehalose.

| | No addition | BSA | PEG | TH | β-CD |
|---|---|---|---|---|---|
| Uniformity of development | Slightly non-uniform | Non-uniform | Non-uniform | Slightly non-uniform | Uniform |

The same trend can be confirmed for various CDs representing cyclic oligosaccharides.

The antigen extraction solution of the present invention, specifically the extraction solution serving as the sample extraction (analyte dilution) solution or the development extraction solution may contain common components such as nitrite compounds (e.g., nitrites), a neutralizing base (e.g., sodium hydroxide), and a buffer (e.g., TRIS). The extraction solution also may contain substances, for example, such as surfactants, ammonium salts, sugars, and pH buffers, having the effect to inhibit side reaction due to biological affinity, or to cancel hydrophobic bonding or electrical interaction; and various additives for inhibiting non-specific reaction, for example, such as proteins and high molecular compounds for promoting antigen-antibody reaction, or inhibiting non-specific reaction.

FIG. 2 represents the effects of various cyclic oligosaccharide compounds on the development solution, and behaviors of these compounds. The experiment represented in FIG. 2 was conducted by retaining cyclodextrin (CD), a representative member of cyclic oligosaccharides, in a nitrous acid-containing portion (2: reagent retaining part (2)) in 0.75 μg/test each, and evaluating each CD with a negative and a positive analyte in a test device containing CD. The cyclodextrin evaluated are β-cyclodextrin ("β-CD" for short), amino-β-cyclodextrin ("Amino-β-CD" for short), 6-0-α-D-maltosyl-β-cyclodextrin a molecular weight of 1459 ("m β-CD" for short), and γ-cyclodextrin ("γ-CD" for short). The results are presented in FIG. 2.

For comparison, a test device containing no CD was fabricated, and compared and evaluated, as shown in FIG. 2.

It can be confirmed that the color was weaker in negative analytes, and was stronger in positive analytes when β-CD and γ-CD were contained in the nitrous acid-containing portion. Thus, it can easily be confirmed that the β-CD family improves sensitivity. However, whether it can inhibit non-specific reaction cannot be ascertained from these data alone. While the nitrous acid generated on the test device is inclined to improve test efficiency, there appears to be a problem that the development solution turns acidic during the development on the test device, and that this probably causes the protein components in the analyte to denature or deposit, and become trapped at the determination line, and induces non-specific reaction.

In order to enable testing without causing deposition of the protein components of the extraction solution or analyte even under acidic conditions, the present invention conducted trial-and-error experiments that added various oligosaccharides, and found that the S/N ratio could be improved by containing CD, a member of cyclic oligosaccharides. Being a member of cyclic oligosaccharides, cyclodextrin (CDs) have a hydrophobic inner structure. It is expected that the foregoing results are due to the function of these compounds to contain various hydrophobic compounds.

The acid used for the extraction solution system retained in the organic acid-containing antigen extracting part (reagent retaining part (3)) of the present invention may be an organic acid, for example, such as acetic acid, tartaric acid, itaconic acid, oxalic acid, succinic acid, citric acid, glycolic acid, chloroacetic acid, fluoroacetic acid, benzoic acid, and benzenesulfonic acid, provided that it reacts with the nitrite compound and generates a nitrous acid, and does not cause denaturation or deposition of proteins or the like present in the test device system.

The acid also may be an immobilized acid, for example, such as polysulfonic acid, polycarboxylic acid and polyacrylic acid, and is not particularly limited. Preferred is an organic acid such as tartaric acid, itaconic acid or citric acid and most preferred is citric acid. These may be used as a mixture.

The proportions of the acid and the nitrite are 0.1 to 4:10 to 100 in terms of a molar ratio. The citric acid is used in preferably 0.1 to 4 μmol, more preferably 0.1 to 3 μmol per test. The nitrite is used in preferably 10 to 100 μmol per test.

The cyclic oligosaccharide used in the present invention may be contained in the sample extraction solution (hereinafter, also referred to, as "development extraction solution") or the analyte dilution solution (hereinafter, also referred to as "analyte treatment solution") for immunochromatography, or in other reagent retaining part in the immunochromatography kit, or in both. The cyclic oligosaccharide may be contained in any place, as long as it can exhibit its function. From the function standpoint, the cyclic oligosaccharide is contained preferably in the analyte treatment solution occurring in an early part of development, or in a part on the upstream side of development.

The immunochromatographic detection method for detecting gram-positive bacteria in an analyte with the immunochromatography kit of the present invention may be provided as a method that includes:

(i) a step of contacting and mixing an analyte with an analyte dilution solution containing a buffer and a surfactant to create an analyte dilution solution mixture;

(ii) a step of supplying the analyte treatment solution mixture to a sample dropping part;

(iii) a step of developing the analyte treatment solution mixture on an immunochromatography medium, and extracting antigens in the gram-positive bacteria with a nitrous acid that generates on the medium through reaction of an organic acid and a nitrite compound present in an antigen extracting part;

(iv) a step of labeling the antigens in a labeling substance retaining part;

(v) a step of moving the labeled antigens on the chromatography medium, and detecting the labeled antigens at a detection part; and (vi) a step of absorbing the analyte treatment solution mixture at an absorption part.

Examples of the non-ionic surfactant that can be used in the analyte dilution solution for immunochromatography, or in the reagent of the immunochromatography kit of the present invention include polyoxyethylenealkyl ether, polyoxyethylene/polyoxypropylene alkyl ether, polyoxyethylene sorbitan fatty acid ester (trade name: "Tween" series), polyoxyethylene p-t-octylphenyl ether (trade name: "Triton" series), polyoxyethylene p-t-nonylphenyl ether (trade name: "Triton N" series), alkyl polyglycolide, fatty acid diethanol amide, and alkyl monoglyceryl ether. The non-ionic surfactant may also be used by being mixed with ionic surfactants or the like, provided that such mixing does not cause adverse effects.

Specifically, the organic acid-containing antigen extracting part in the immunochromatography kit of the present invention requires a surfactant to achieve uniform development. However, it is known that containing a surfactant is detrimental to the preservation stability of the antigen extracting part. To solve this problem antigen extracting parts containing various surfactants were produced, and tested under severe conditions (80° C., 12 hours). As a result, the following surfactants were found to be preferable: Polyoxyethylene p-t-octylphenyl ether (trade name: "Triton" series), for example, polyoxyethylene (10)-p-t-octylphenyl ether (TritonX-100 (trade name), HLB=13.5), "Triton X-114" (trade name) (HLB=12.4), and polyoxyethylene p-t-nonylphenyl ether (trade name: "Triton N" series). Most preferred is polyoxyethylene (10)-p-t-octylphenyl ether (Triton X-100 (trade name)).

The non-ionic surfactant used in the analyte dilution solution or in the immunochromatography reagent of the present invention is contained in 0.01 to 10 weight %. The non-ionic surfactant may be contained in an immunochromatography reagent in preferably 0.05 to 5 weight %. An accurate determination is possible with a content of 0.01 weight % or more. With a content of 0.05 weight % or more, non-specific reaction can be inhibited, and an accurate determination is possible. A content of 10 weight % or less is preferable in terms of inhibiting non-specific reaction while being economical.

Typical examples of the salt used in immunochromatography reagents such as the extraction development solution, and the analyte treatment solution of the present invention include sodium chloride, potassium chloride, calcium chloride, and magnesium chloride. The preferred salt is sodium chloride.

The concentration of the salt used in immunochromatography reagents such as the extraction development solution of the present invention ranges from 1 mM to 500 mM, preferably 5 mM to 200 mM, more preferably 10 mM to 50 mM. A sufficient protein extracting effect can be obtained with a concentration of 1 mM or more. A concentration of 500 mM or less is economical.

The salt used in the immunochromatography reagent of the present invention may be used either alone or as a mixture of two or more.

The buffer used in the extraction development solution of the present invention is not particularly limited, as long as its effect (buffering effect) is not seriously affected by concentration changes due to addition of a sample, or evaporation or dilution of a sample, or by inclusion of some foreign objects from outside.

Example of the buffer used in the present invention include phosphate buffer (phosphoric acid+sodium phosphate), acetate buffer (acetic acid+sodium acetate), citrate buffer (citric acid+sodium citrate), borate buffer, trishydrochloride buffer (tris(hydroxymethyl)aminomethane+hydrochloric acid), TE buffer (tris+ethylenediaminetetraacetic acid), TAE buffer (tris+acetic acid+ethylenediaminetetraacetic acid), TBE buffer (tris+boric acid+ethylenediaminetetraacetic acid) or HEPES buffer (2-[4-(2-hydroxyethyl)-1-piperazinyl]ethanesulfonic acid), and Bicine buffer (N,N-bis(2-hydroxyethyl)glycine buffer). Preferred examples include phosphate buffer, trishydrochloride buffer, and acetate buffer, More preferred is trishydrochloride buffer. In the immunochromatographic detection system of the present invention, the buffer is not particularly limited, and two or more buffers may be used, provided that it does not cause adverse effects.

The concentration of the buffer used in the present invention is preferably 10 to 500 mM, more preferably 10 to 300 mM, further preferably 30 to 100 mM. With a concentration of 10 mM or more, a sufficient buffering effect can be obtained, and deposition of the protein components, and agglutination of the labeling particles can be sufficiently inhibited. A concentration of 500 mM or less is economical. The buffer has an optimum pH range of 7.1 to 9.8.

Without being limited, it is possible and effective to add one or more additives that are known to inhibit side reaction due to biological affinity, and non-specific reaction to the immunochromatography reagent of the present invention. Such additives may be additives for promoting antigen-antibody reaction or inhibiting non-specific reaction. Examples include proteins (for example, such as bovine serum albumin, gelatin, and casein), high molecular compounds (for example, such as polyethylene glycol, methyl cellulose, polyvinylpyrrolidone, polyvinyl alcohol, and dextran), ionic surfactants or polyanions (for example, such as dextransulfuric acid, heparin, polystyrene sulfonate, and chondroitin sulfate), and anti-microbial agents.

Without being limited, it is also possible and effective to retain one or more of such proteins, high molecular compounds, ionic surfactants, polyanions, and anti-microbial agents for promoting antigen-antibody reaction or reducing non-specific reaction on a migration pathway of the mobile phase on the chromatography medium constituting the stationary phase.

The concentration of the additive contained in the immunochromatography reagent composition of the present invention is preferably 0.01 to 20 weight %, more preferably 0.1 to 10 weight %, further preferably 0.5 to 5 weight %. With a concentration of 0.01 weight % or more, non-specific reactions can be inhibited, and an accurate determination is possible. A, concentration of 20 weight % or less is economical.

The immunochromatography reagent of the present invention has optimum use as a development solution, and also may preferably be used as an analyte sample dilution solution. The immunochromatography reagent is not limited to these uses, and may be used in an embodiment in which the components of the immunochromatography reagent are provided on a migration pathway of the mobile phase on the chromatography medium.

When the immunochromatography reagent is used as a development solution or a dilution solution, water is typically used as solvent, and a buffer, a protein, a salt, and a non-ionic surfactant are added thereto. These may be added in any order, and may be added simultaneously. When the immunochromatography reagent is used as a development solution or a dilution solution, the solution may be supplied and dropped on the sample pad (sample dropping part) to develop after being mixed with a detection sample (analyte). Alternatively, the development solution may be supplied and dropped on a sample pad (sample dropping part) to develop after supplying and dropping the sample (analyte) on the sample pad (sample dropping part).

When the immunochromatography reagent of the present invention is used by being provided on a migration pathway of the mobile phase on the immunochromatography medium, as an embodiment, the immunochromatography reagent may be supported or retained in the sample pad by using, for example, a method that applies the reagent to the sample pad (sample dropping site), or impregnates the sample pad with the reagent in the immunochromatography device, followed by drying.

The immunochromatography reagent of the present invention also may be retained or supported on the immunochromatography medium in an embodiment in which the reagent is retained in an additive (reagent) retaining part provided at any location between the end of the sample dropping part and the absorption part. The immunochromatography reagent also may be retained or supported on, for example, the sample dropping part, the labeling substance retaining part, or the immunochromatography medium.

The detection target of the present invention is not particularly limited, as long as a substance that specifically binds to the detection target, for example, such as in antigen-antibody reaction, is present, or can be produced. The detection target may be a complete antigen that is antigenic by itself, or may be an antigen, such as a hapten (incomplete antigen), that is not antigenic by itself but becomes antigenic after chemical transformation.

The substance that is present, or that can be produced for specific binding with the detection target may be a monoclonal antibody or a polyclonal antibody. The detection target of the present invention is a polysaccharide antigen, specific to the detection target, that can be extracted with the generated nitrous acid. Examples include gram-positive bacteria having a thick peptidoglycan layer. Among them, cocci are preferred, and bacterial antigens such as streptococcus antigens are particularly preferred.

The optimum analyte in the present invention is nasal discharge, a swab from nasal cavity, a swab from pharynx, or phlegm. These analytes are subjected to a dilution treatment in advance with the analyte dilution solution of the present invention, and supplied onto the test device for extraction. The streptococcus antigen collected from a respiratory disease patient or the like can thus be appropriately detected as a substance to be detected.

The immunochromatography kit of the present invention is configured from an analyte treatment solution, a sample dropping part, an antigen extracting part, a labeling substance retaining part, an immunochromatography medium having a detection part, and an absorption part, and detects gram-positive bacteria in a sample with the immunochromatography medium. The cyclic oligosaccharide and the nitrite compound are contained in the analyte treatment solution and/or the sample dropping part by being contained therein either alone or together. The immunochromatography kit also includes an antigen extraction site where a nitrous acid generates through reaction between the nitrite compound and the orzanic acid retained in the antigen extracting part.

The immunochromatography kit contains the cyclic oligosaccharide preferably 0.1 to 5 μg per kit. In the immunochromatography kit, the sample dropping part (2) and the antigen extracting part (3) constituting the kit are disposed upstream of the labeling substance retaining part (4) relative to the direction of reagent development. Preferably, the organic acid-containing antigen extracting part (reagent retaining part (3)) retains citric acid with a citrate.

A test kit used for the immunochromatography method that detects a substance to be detected in an analyte (hereinafter, simply "immunochromatography kit") has a known structure, and the operation and the detection technique are known.

An analyte sample obtained after a dilution treatment of an analyte using the analyte treatment solution of the present invention is dropped into the sample pad of a conventional immunochromatography kit, and developed toward the absorption site on the immunochromatography medium to extract the antigen in the analyte as the sample develops. Through antigen-antibody reaction, tests such as detection and quantification of the substance to be detected in the analyte can be conducted.

The immunochromatography kit is described below.

The immunochromatography kit typically includes a chromatography medium (1) (having a "detection part (determining part)"), a sample dropping part (2) (also referred to as "sample pad (2)" or "reagent retaining part (2)"), an antigen extracting part (3) (also referred to as "organic acid-containing antigen extracting part (3)" or "reagent retaining part (3)"), a labeling substance retaining part (4) (also referred to as conjugate pad (4)), an absorption part (5) (also referred to as "development rate control part (5)"), an analyte dilution solution (extraction solution) (6), and a backing sheet (7).

The immunochromatography device is described below.

FIGS. 1, (a) and (b) represent the structure of a kit devised to improve particularly antigen extraction efficiency in implementing the components of the immunochromatography reagent of the present invention on the immunochromatography medium, specifically in properly implementing the immunochromatographic detection method. The kit is described below with reference to FIGS. 1, (a) and (b).

The kit shown in FIG. 1 has a structure configured from the constituent elements 1: a chromatography medium (1), 2: a reagent dropping part (reagent retaining part) (2) (or, collectively, sample pad), 3: an antigen extracting part (reagent retaining part) (3) (or, collectively, organic acid-containing antigen extracting part (3)), 4: a labeling substance retaining part (4) (or, collectively, conjugate pad), 5: an absorption part (5), 6: an analyte dilution solution (extraction solution) (6), and 7: a backing sheet (7). The present invention is an immunochromatography kit of a structure configured from at least the foregoing elements 1 to 5.

The present invention found that the order of these constituent elements has effect on performance. The following illustrates the order of the constituent elements of the structure, and its effect on development, compared in respect to the following two points.

| Structure of the present invention (1) | 2 3 4 1 5 | Desirable development |
| Comparative structure (2) | 3 2 4 1 5 | Development failure |

Randomly changing the order of the constituent elements 1 to 5 in the manner exemplified above affects the behavior, particularly the development. The most preferred embodiment in the combination of these constituent elements is the order of development represented in FIGS. 1(a) and (b) of the present invention. When the development is not of great concern, the kit may have a structure with these constituent elements disposed in a different order.

Meanwhile, the immunochromatography kit represented in FIGS. 1(a) and (b) is basically a testing instrument with the constituent elements shown in FIG. 1. Omission of an element, particularly 3: antigen extracting part (3) necessitates the complicated task of preparing a nitrous acid at the time of use, and works against smooth testing.

The present inventors thus found that the kit of the present invention represented in FIG. 1 has great functionality in terms of test performance and test handling.

The sample dropping part (2) and the antigen extracting part (3) are configured from a porous sheet, such as glass filter paper, of a property that allows a sample to be quickly absorbed but retains the sample only weakly so as to allow it to quickly migrate to the reaction part.

The sample dropping part (2) may contain a nitrite that generates a nitrous acid upon reacting with the organic acid contained in the antigen extracting part (3). However, a nitrite may be contained in the analyte dilution solution (6) instead, or in both the sample dropping part (2) and the analyte dilution solution (6). The nitrite can effectively serve its function when contained upstream of the site containing the organic acid relative to the direction of development.

The cyclic oligosaccharide may be contained in the analyte dilution solution (6). However, the cyclic oligosaccharide may be contained in the sample dropping part (2) instead, or in both the analyte dilution solution (6) and the sample dropping part (2). The cyclic oligosaccharide can effectively serve its function when contained upstream of the site containing the organic acid relative to the direction of development.

The antigen extracting part (3) serves as the antigen extracting part, and contains an organic acid for this purpose. The antigen extracting part (3) also contains a non-ionic surfactant Triton X-100 (trade name) or Triton X-114 (trade name) to achieve uniform development. Preservation stability also improved.

A labeling reagent as a conjugate of a reagent component with a labeling component is retained in the labeling substance retaining part (4). Examples of the labeling component include metal colloid particles, latex particles, enzymes, and fluorescence compounds. Among them, a metal colloid particle is optimum. The reagent component is a particle or a molecule capable of recognizing the analyte. The reagent component is preferably a monoclonal antibody or a polyclonal antibody, or a fragment thereof (second reagent).

Preferred as the metal colloid particles are any simple particles or composite particles of noble metals such as silver, platinum, germanium, rhodium, and palladium. Gold, with its sensitivity to hue changes, is most suitable. Concerning the state of metal colloid particles, preferred for use as the metal colloid particles are those having an average particle size of 1 to 500 nm, preferably 10 to 250 nm, more preferably about 35 to 100 nm, and the metal colloid particles are contained in preferably 0.0001 to 0.08 weight %, preferably about 0.002 to 0.06 weight % with respect to the medium.

As used herein, "gold nanoparticles" means a range of nano sized gold colloidal particles having the foregoing average particle size ranges. For immunoassay, platinum colloidal particles may be supported on surfaces of gold colloidal particles to prepare gold colloid composite particles, taking into consideration variables such as the particle size, the particle size distribution, and the color tone of the gold colloids, and may be used as immunoassay labels, or to improve its usefulness as a protein dyeing agent. In addition, measurement sensitivity can be improved by using a colloidal gold label amplifier, or a sensitizer as it is also called, that has a functional group capable of binding to the metal particle surface, and a reactive group capable of binding to the antibody.

The chromatography medium (1) is a medium with a detection site fabricated on a membrane support. The membrane support is not particularly limited, so long as it can absorb a sample analyte by means of capillary action, and can cause the analyte to migrate. For example, the support may be selected from the group consisting of nitrocellulose, cellulose acetate, nylon, polyether sulfone, polyvinyl alcohol, polyester, glass fiber, polyolefin, cellulose, and a synthetic polymer made of mixed fibers of these.

At the detection site, a monoclonal antibody or a polyclonal antibody, or a fragment thereof (first reagent) is supported and immobilized on a nitrocellulose sheet.

A filter paper made of a glass fiber, a cellulose fiber, or other such materials capable of quickly absorbing an excess of sample is commonly used for the absorption part (5). It is, however, more preferable to use materials that are capable of retaining the absorbed liquid without causing a backflow (JP-A-2012-189346).

The backing sheet (7) is a substrate. The backing sheet (7) has an adhesive agent or an adhesive tape applied or attached to one of its surfaces to make the surface adhesive. The sample dropping part (2), the antigen extracting part (3), the labeling substance retaining part (4), the chromatography medium (1) having a detection part, and the absorption part (5) bonded, either partially or as a whole, to this adhesive surface. The backing sheet (7) is not limited to a particular substrate, as long as it is made impermeable to the sample liquid and moisture-impermeable by the adhesive agent.

Either or both of the reagent component (first reagent) used for the detection site, and the reagent component (second reagent) used for the labeling reagent may be monoclonal antibodies or polyclonal antibodies.

The monoclonal antibodies, the polyclonal antibodies, or fragments thereof are known and available, and may be prepared using known methods. Examples of antibody-producing animal species include humans, mice, rats, rabbits, goat, and horses. The immunoglobulin may be any of IgG, IgA, IgE, and IgD.

Examples of the present invention use rabbit-derived anti-streptococcus polyclonal antibodies for both the reagent component (second reagent) used for the labeling substance retaining part (4), and the reagent component (first reagent) used for the detection site. However, this should not be construed as a limitation.

The following is an overview of the principle of a determination using a typical kit configuration.

1. An analyte dilution solution mixture prepared by diluting an analyte (sample) with the analyte dilution solution (6) is dropped on the sample dropping part (2) in a predetermined amount (typically, 0.1 to 2 ml). Upon being dropped, the analyte dilution solution mixture becomes quickly absorbed by the sample dropping part (2), and quickly starts to migrate. Also, the nitrite- and cyclodextrin-containing reagent composition dried and retained in the sample dropping part (2) becomes dissolved in the water component of the analyte dilution solution mixture, and starts to migrate with the analyte (sample).

2. The analyte dilution solution mixture containing the dissolved nitrite first migrates to the antigen extracting part (3). Here, the organic acid dried and retained in the antigen extracting part (3) contacts and reacts with the nitrite dissolved in the incoming analyte dilution solution mixture, and generates a nitrous acid. The nitrous acid extracts the polysaccharide on bacteria surface when streptococcus is present in the analyte (sample).

3. The analyte dilution solution mixture containing the generated nitrous acid uniformly and smoothly migrates to the labeling substance retaining part (4). The labeling reagent (second reagent) retained in the labeling substance retaining part (4) becomes dissolved in the water component of the analyte dilution solution mixture as the analyte dilution solution mixture passes the labeling substance retaining part (4), and migrates with the analyte (sample).

4. Subsequently, the labeling reagent dissolved in the water component of the analyte dilution solution mixture passes the detection site on the chromatography medium (1). Here, the immunochromatography reagent composition dissolved in the analyte dilution solution mixture inhibits non-specific binding reaction, and the substance to be detected (for example, polysaccharide), when present in the analyte dilution solution mixture, undergoes an antigen-antibody specific binding reaction whereby the substance to be detected specifically reacts and binds to the antibody supported and immobilized at the detection site so that the substance is sandwiched between the antibody and the labeling reagent. In response, the detection part produces a color. When the substance to be detected (for example, polysaccharide) is absent in the analyte sample, the labeling reagent dissolved in the water component of the analyte dilution solution mixture does not undergo a specific binding reaction upon passing the detection part on the chromatography medium (1), and the detection site does not produce a color.

5. Finally, the water component in the analyte dilution solution mixture migrates to the absorption part (5).

The presence or absence of a substance to be detected (for example, polysaccharide) in an analyte (sample) can be accurately determined in the manner described above.

EXAMPLES

The effectiveness of the present invention is described below using Examples. The present invention, however, is not limited to the examples. The present invention is immunochromatography kit that includes a sample dropping part (2) containing sodium nitrite, an antigen extracting part (3) containing citric acid, and an absorption part (5) comprised of a development rate control member for optimizing extraction efficiency (water absorption amount: 80 to 200 mg/cm$^2$).

EXAMPLES

Example 1

(1) Fabrication of Determining Part on Chromatography Medium (1)

A nitrocellulose sheet (manufactured by Millipore, trade name: HF120, 250 mm×25 mm) was used as membrane. A rabbit-derived anti-streptococcus polyclonal antibody (first antibody) was diluted in a concentration of 1.0 mg/ml with a 10 mM phosphate buffer (pH 7.4) containing 5 mass % of isopropanol, and 150 μL of the diluted solution was applied onto the membrane over a width of 1 mm using an antibody applicator (manufactured by BioDot). The solution was dried at 50° C. for 30 min, and dried overnight at room temperature to fabricate a determining part on the chromatography medium (1).

(2) Production of Labeling Substance Solution

A rabbit-derived anti-streptococcus polyclonal antibody (second antibody; 0.1 mL) diluted in a concentration of 0.1 mg/mL with phosphate buffer (pH 7.4) was added to 0.5 mL of a gold colloid suspension (manufactured by Tanaka Kikinzoku Kogyo: average particle size 40 nm), and the mixture was allowed to stand at room temperature for 10 min. Subsequently, after adding 0.1 mL of phosphate buffer (pH 7.4) containing 10 mass % of bovine serum albumin, the mixture was thoroughly stirred, and centrifuged at 8000×g for 15 min. After removing the supernatant, 0.1 mL of phosphate buffer (pH 7.4) containing 1 mass % of bovine serum albumin was added to produce a labeling substance solution.

(3) Fabrication of Sample Dropping Part (Reagent Retaining Part) (2) Containing Sodium Nitrite and Cyclic Oligosaccharide An aqueous solution (0.6 mL) containing 2 μmol of β-cyclodextrin with 1 mmol of sodium nitrite was applied to a 12×100 mm glass fiber conjugate pad (manufactured by Merck), and freeze dried to fabricate the sample dropping part (reannt retaining part) (2).

(4) Fabrication of Antigen Extracting Part (Reagent Retaining Part) (3) Containing Citric Acid An aqueous solution (0.6 mL) of 1.7 mass % non-ionic surfactant Triton-X100 containing 50 μmol of citric acid was applied to a 12×100 mm glass fiber conjugate pad (manufactured by Merck), and freeze dried to fabricate the antigen extracting part (reagent retaining part) (3).

(5) Fabrication of Test Piece for Immunochromatography

A mixture of the labeling substance solution fabricated as above (200 μl) and a phosphate buffer (pH 9.0) containing 100 μl of a 25 mass % trehalose aqueous solution and 80 of 5 mass % casein (final concentration: 1 mass %) was uniformly added to a 12×100 mm glass fiber pad (manufactured by Millipore), and dried with a vacuum drier to fabricate the labeling substance retaining part (4). The absorption part (5) for absorbing the developed sample and the labeling substance, the chromatography medium (1) with the determining part fabricated as above, the labeling substance retaining part (4), the sample dropping part (2), and the antigen extracting part (3) were attached to a substrate comprised of the backing sheet (7) in the order presented in Table 1 from the upstream side in the direction of immunochromatography development (development direction is from left to right). The substrate was then cut into a 5-mm width with a cutter to obtain a test piece for immunochromatography.

(6) Production of Analyte Dilution Solution

An analyte containing 0.5 mass % of Tweet 20, 0.6 mass % of polyvinylpynolidone (average molecular weight 360,000), and 20 mM of tris buffer solution (pH 8.0) containing 1 mass % of bovine serum albumin and 150 mM sodium chloride was diluted, and added to the immunochromatography test piece to obtain an analyte dilution solution for development.

(7) Measurement

The presence or absence of the antigen streptococcus in the analyte was measured according to the method described below, using the immunochromatography test piece and the analyte dilution solution produced above. Specifically, the analyte dilution solution without antigen was used as a negative analyte sample, and the negative analyte sample with $2\times10^6$ org/mL of deactivated group A β-hemolytic streptococcus (streptococcus) was used as a positive analyte sample.

The negative analyte sample and the positive analyte sample (1.50 μL each) were added to the upstream end of the immunochromatography test piece relative to the direction of development, specifically, on the reagent dropping part (2) in Examples 1 and 2, on the antigen extracting part (3) in Comparative Examples 1 and 2, and on the labeling substance retaining part (4) in Comparative Example 3 and Example 3. The samples were allowed to develop, and visually inspected for determination after 15 min. Samples showing a red line at the test line were determined as "+". Samples showing a clear red line were determined as "++". Samples showing a red line but only in a very pale color were determined as "±". Samples with no red line were determined as "−". As an evaluation of development, samples were determined as having failed to develop when the development solution did not flow onto the chromatography medium, when the development solution developed on the chromatography medium but was not accompanied by a flow of the gold nanoparticle-conjugated reagent, and when the solution developing on the chromatography medium had an irregular shape at the leading end of the flowing solution. Samples with no such failure were determined as desirable. The results are presented in Table 1.

By using the chromatography kit of Example 1 in the same configuration, the test device was evaluated with negative and positive analytes using γ-cyclodextrin, amino-β-cyclodextrin, and m β-cyclodextrin, and without using cyclodextrin in the reagent dropping part (2), instead of using β-cyclodextrin (hereinafter, simply "β-CD"). These CDs were retained in the nitrous acid-containing part in 0.75 μg/test each.

For comparison, a test device containing no CD was produced, and evaluated. The results are presented in FIG. 2. The tests were performed under the following conditions.

Positive: $4\times10^5$ org/mL streptococcus (determination time 8 min)

Negative: development solution (determination time 30 min)

As is clear from the results shown in FIG. 2, retaining β-CD and γ-CD in the nitrous acid-containing part resulted in weak color production in negative analytes, and improved color production in positive analytes. Sensitivity improved with the β-CD derivatives, but the color production in the negative analyte was higher than in samples using β-CD and γ-CD, and the S/N ratio was smaller than in these samples using β-CD and γ-CD.

TABLE 1

| | Attachment order* (from upstream side relative to development direction) | Antigen amount in positive analyse | Development result | Determination |
|---|---|---|---|---|
| Ex. 1 | 2-3-4-1-5 | $2\times10^6$ org/mL | Desirable | + |
| Ex. 2 | 2-4-3-1-5 | | Desirable | + |
| Com. Ex. 1 | 3-2-4-1-5 | | Failure | |
| Com. Ex. 2 | 3-4-2-1-5 | | Failure | |
| Com. Ex. 3 | 4-3-2-1-5 | | Failure | |
| Ex. 3 | 4-2-3-1-5 | | Desirable | + |

In the table, the numbers 1 to 5 denote 1: chromatography medium (1), 2: sample dropping part (2), 3: antigen extracting part (3), 4: labeling substance retaining part (4), and 5: absorption part (5).

As can be seen from these results, the protein component in the sample was not affected by the acid, and the development was desirable in Examples 1 to 3 in which the antigen extracting part (3) containing citric acid was on the downstream side of the reagent dropping part (2) relative to the direction of development.

Development failed in Comparative Examples 1 to 3 in which the antigen extracting part (3) containing citric acid was on the upstream side of the reagent dropping part (2) relative to the direction of development, presumably because of the acid-induced deposition of the protein component in the sample causing clogging or other problems. These test results show that it is necessary to dispose the reagent dropping part (2) on the upstream side of the antigen extracting part (3) relative to the direction of development.

Examples 4 to 12

Tests were performed with sodium nitrite, cyclic oligosaccharide, and citric acid in the amounts (amounts per test) given in Table 2, using the same procedures used in Example 1. The positive analyte contained $2\times10^6$ org/mL, of deactivated streptococcus per test, and was used in 150 μL.

The samples were evaluated using the same criteria by visual inspection. The results are presented in Table 2.

Example 13

Tests were performed using the same procedures used in Example 1, except that the antigen extracting part (3) contained tartaric acid, instead of citric acid. The samples were evaluated using the same criteria by visual inspection. The results are presented in Table 2.

Example 14

Tests were performed using the same procedures used in Example 1, except that the reagent dropping part (2) did not contain sodium nitrite, and that potassium nitrite (50 μmol/test) was added to the analyte dilution solution. The samples were evaluated using the same criteria by visual inspection. The results are presented in Table 2.

Example 15

Tests were performed using the same procedures used in Example 1, except that the reagent dropping part (2) did not contain β-cyclodextrin, and that 0.1 μmol of β-cyclodextrin was added to the analyte dilution solution, and the antigen extracting part (3) contained itaconic acid, instead of citric acid. The samples were evaluated using the same criteria by visual inspection. The results are presented in Table 2.

Examples 14 and 15 represent the implementation in which a nitrite or a cyclic oligosaccharide is retained in the analyte dilution solution.

Example 16

Tests were performed using the same procedures used in Example 1, except that the reagent dropping part (2) did not contain β-cyclodextrin or sodium nitrite, and that 50 μmol of sodium nitrite and 0.1 μmol of β-cyclodextrin were added to the analyte dilution solution. The samples were evaluated using the same criteria by visual inspection. The results are presented in Table 2.

Example 16 represents the implementation in which a nitrite and a cyclic oligosaccharide are retained in the analyte dilution solution.

Examples 17 to 21

Tests were performed using the same procedures used in Example 4, except that citric acid was used as a mixture of citric acid and trisodium citrate in the proportions given in Table 3. The samples were evaluated using the same criteria by visual inspection. The results are presented in Table 3.

TABLE 3

| Citric acid:trisodium citrate | | Analyte | Determination (N = 5) | | | | |
|---|---|---|---|---|---|---|---|
| Ex. 4 | 1:0 | Positive analyte | + | + | ++ | + | + |
| | | Negative analyte | – | – | – | – | – |
| Ex. 17 | 5:1 | Positive analyte | + | ++ | ++ | ++ | + |
| | | Negative analyte | – | – | – | – | – |
| Ex. 18 | 4:1 | Positive analyte | ++ | + | ++ | ++ | ++ |
| | | Negative analyte | – | – | – | – | – |
| Ex. 19 | 3:2 | Positive analyte | ++ | ++ | ++ | + | ++ |
| | | Negative analyte | – | – | – | – | – |
| Ex. 20 | 2:3 | Positive analyte | ++ | ++ | ++ | ++ | ++ |
| | | Negative analyte | – | – | – | – | – |
| Ex. 21 | 1:3 | Positive analyte | + | ++ | ++ | + | ++ |
| | | Negative analyte | – | – | – | – | – |

As clearly demonstrated by these results, it was preferable to use citric acid as a mixture of citric acid and an alkali metal salt of citric acid, and that these should be used in proportions of preferably 5:1 to 1:3, optimally 4:1 to 2:3 in an immunochromatographic streptococcus test. With this

TABLE 2

| | Sodium nitrite amount μmol/test | Cyclic oligosaccharide kind and amount: (μmol/test) | Citric acid amount μmol/test | Analyte | Determination (N = 5) | | | | |
|---|---|---|---|---|---|---|---|---|---|
| Ex. 4 | 50 | β-Cyclodextrin (0.1) | 1 | Positive analyte*[1] | + | + | ++ | + | + |
| | | | | Negative analyte | – | – | – | – | – |
| Ex. 5 | 10 | β-Cyclodextrin (0.02) | 1 | Positive analyte*[1] | + | + | + | + | + |
| | | | | Negative analyte | – | – | – | – | – |
| Ex. 6 | 100 | β-Cyclodextrin (0.1) | 1 | Positive analyte*[1] | + | + | + | + | + |
| | | | | Negative analyte | – | – | – | – | – |
| Ex. 7 | 50 | Amino-β-Cyclodextrin*[2] (0.1) | 1 | Positive analyte*[1] | + | + | + | + | + |
| | | | | Negative analyte | – | ± | – | – | – |
| Ex. 8 | 50 | m β-Cyclodextrin*[3] (0.1) | 1 | Positive analyte*[1] | + | ++ | ++ | + | ++ |
| | | | | Negative analyte | – | – | ± | – | – |
| Ex. 9 | 50 | γ-Cyclodextrin (0.1) | 0.1 | Positive analyte*[1] | ++ | + | ++ | ++ | + |
| | | | | Negative analyte | – | – | – | – | – |
| Ex. 10 | 50 | γ-Cyclodextrin (0.1) | 0.25 | Positive analyte*[1] | ++ | ++ | ++ | ++ | ++ |
| | | | | Negative analyte | – | – | – | – | – |
| Ex. 11 | 50 | γ-Cyclodextrin (0.1) | 1 | Positive analyte*[1] | ++ | + | ++ | + | ++ |
| | | | | Negative analyte | – | – | – | – | – |
| Ex. 12 | 50 | γ-Cyclodextrin (0.5) | 3 | Positive analyte*[1] | + | + | + | + | + |
| | | | | Negative analyte | – | – | – | – | – |
| Ex. 13 | 50 | γ-Cyclodextrin (0.5) | 4*[4] | Positive analyte*[1] | + | + | ± | ± | + |
| | | | | Negative analyte | – | – | – | – | – |
| Ex. 14 | 50*[5] | β-Cyclodextrin (0.1) | 1 | Positive analyte*[1] | + | + | + | + | + |
| | | | | Negative analyte | – | – | – | – | – |
| Ex. 15 | 50 | β-Cyclodextrin (0.1) | 1*[6] | Positive analyte*[1] | + | ± | + | ± | + |
| | | | | Negative analyte | – | – | – | – | – |
| Ex. 16 | 50 | β-Cyclodextrin (0.1) | 1 | Positive analyte*[1] | + | ± | + | + | + |
| | | | | Negative analyte | – | – | – | – | – |

*[1]The positive analyte contained 2 × 10^6 org/mL of deactivated *streptococcus* per test, and was used in 150 μL.
*[2]Amino-β-cyclodextrin: 3A-amino-3A-deoxy-(2AS,3AS)-β-cyclodextrin hydrate
*[3]m β-Cyclodextrin: 6-0-α-D-maltosyl-β-cyclodextrin (molecula weight 1459)
*[4]Tartaric acid was used in place of citric acid
*[5]Potassium nitrite was used in place of sodium nitrite
*[6]Itaconic acid was used in place of citric acid Sodium nitrite is used in preferably 10 to 100 μmol per test.

implementation, there will be no deposition of the protein component, or agglutination of antibody sensitized gold colloids, and an accurate determination is possible with an improved S/N ratio while maintaining a high development rate.

Example 22

Tests were performed in the same manner as in Example 4, except that 1 mass % of casein was used in place of the bovine serum albumin in the production of analyte dilution solution. The negative analyte did not yield a false positive result, and there was no development failure caused by deposition due to the reaction between casein and nitrous acid. The detection sensitivity for the positive analyte was as high as that observed in Example 4. (The results were "+" or higher in all positive analytes in five repeated tests.)

As clearly demonstrated by these results, it was preferable to use sodium nitrite in 10 to 100 µmol per test, and use citric acid in preferably 0.1 to 4 µmol, more preferably 0.1 to 3 µmol per test in an immunochromatographic streptococcus test. It was also found that the cyclic oligosaccharide should be used in preferably 0.02 to 0.5 µmol per test, and that the cyclic oligosaccharide, when used in this range, produces the notable effects that there is no deposition of the protein component or agglutination of antibody sensitized gold colloids, and that an accurate determination is possible with a high development rate and a high S/N ratio.

INDUSTRIAL APPLICABILITY

The present invention can be used for easy and quick testing and diagnosis of gram-positive bacteria, particularly group A β-hemolytic streptococcus, which is one of respiratory infections. This desirable advantage of the invention enables high-sensitivity quick clinical testing not only by those in a hospital or clinic but by untrained individuals, and the invention has potential use for early diagnosis or treatment of infected individuals. The invention also does not require preparing the unstable compound nitrous acid at the time of use, so that there is no need to perform the complicated nitrous acid generating step of reacting a nitrite with an acidic solution at the time of use for each testing. This improves not only the handling, the test efficiency, and the test accuracy of the kit of the present invention, but the efficiency and the power efficiency of testing. The invention can thus greatly contribute to the development of industrial fields involving test institutions and industrial fields associated with medicine.

While the present invention was described in detail using certain embodiments, it would be apparent for those skilled in the art that various changes and modifications can be made without departing from the spirit and scope of the present invention. The present application is based on Japanese Patent Application (Japanese Patent Application No. 2013-464819) filed Aug. 8, 2013, the entire contents of which are hereby incorporated by reference.

REFERENCE SIGNS LIST

1 Chromatography medium (1)
2 Sample dropping part (2) (reagent retaining part (2))
3. Antigen extracting part (3) (reagent retaining part (3))
4 Labeling substance retaining part (4)
5 Absorption part (5)
6 Analyte dilution solution (extracting solution) (6)
7 Backing sheet

The invention claimed is:

1. An immunoassay method for detecting a polysaccharide antigen present on a cell surface of a gram-positive bacterium in a sample, the method comprising the following steps (1) to (4) sequentially performed in the presence of a cyclic oligosaccharide:
   (1) contacting the sample with a nitrite compound,
   (2) reacting the nitrite compound with an organic acid to produce nitrous acid,
   (3) extracting a polysaccharide antigen present on the cell surface of the gram positive bacterium in the sample with the nitrous acid, and
   (4) detecting the polysaccharide antigen with an antibody.

2. The immunoassay method according to claim 1, wherein steps (1)-(4) are performed using an immunoassay device with a sample addition part, an antigen extracting part that contains the organic acid, a labeling substance retaining part, a chromatographic medium part, and a detection part; and
   wherein step (1) further comprises preparing the sample by bringing an analyte into contact with an analyte dilution solution, and supplying the sample to the sample addition part of the immunoassay device; wherein the cyclic oligosaccharide, the nitrite compound, or mixtures thereof are contained in any one or both of the analyte dilution solution and the sample addition part; and
   wherein the nitrous acid produced in step (2) is generated by the reaction of the organic acid and the nitrite compound in the antigen extracting part.

3. The immunoassay method according to claim 1, wherein the cyclic oligosaccharide is α-cyclodextrin, β-cyclodextrin, γ-cyclodextrin, or a derivative thereof.

4. The immunoassay method according to claim 2 wherein the nitrite compound is an organic nitrite.

5. The immunoassay method according to claim 2 wherein the organic acid is an organic carboxylic acid.

6. The immunoassay method according to claim 1, wherein the extraction is performed under a pH condition with a pH of 6.5-7.0.

7. The immunoassay method according to claim 1, wherein the gram-positive bacterium is a hemolytic streptococcus.

8. The immunoassay method according to claim 2 wherein the nitrite compound is an organic nitrite compound.

* * * * *